United States Patent
Lee et al.

(10) Patent No.: US 11,499,019 B2
(45) Date of Patent: Nov. 15, 2022

(54) CURABLE COMPOSITION

(71) Applicant: LG CHEM, LTD., Seoul (KR)

(72) Inventors: Jin Kyu Lee, Daejeon (KR); Seung Hee Lee, Daejeon (KR); Sang Woo Kim, Daejeon (KR); Sang Bum Ahn, Daejeon (KR)

(73) Assignee: LG CHEM, LTD., Seoul (KR)

( * ) Notice: Subject to any disclaimer, the term of this patent is extended or adjusted under 35 U.S.C. 154(b) by 1023 days.

(21) Appl. No.: 16/305,111

(22) PCT Filed: Nov. 29, 2017

(86) PCT No.: PCT/KR2017/013782
§ 371 (c)(1),
(2) Date: Nov. 28, 2018

(87) PCT Pub. No.: WO2018/101728
PCT Pub. Date: Jun. 7, 2018

(65) Prior Publication Data
US 2020/0325286 A1     Oct. 15, 2020

(30) Foreign Application Priority Data
Nov. 30, 2016    (KR) ........................ 10-2016-0162151

(51) Int. Cl.
| | |
|---|---|
| *C08J 3/28* | (2006.01) |
| *C08K 3/013* | (2018.01) |
| *C07C 255/54* | (2006.01) |
| *C08G 73/02* | (2006.01) |
| *C08K 3/08* | (2006.01) |
| *C08K 3/22* | (2006.01) |
| *C08F 2/46* | (2006.01) |

(52) U.S. Cl.
CPC ............... *C08J 3/28* (2013.01); *C07C 255/54* (2013.01); *C08F 2/46* (2013.01); *C08G 73/024* (2013.01); *C08K 3/013* (2018.01); *C08K 3/08* (2013.01); *C08K 3/22* (2013.01); *C01P 2006/42* (2013.01); *C08J 2379/02* (2013.01); *C08K 2201/001* (2013.01); *C08K 2201/005* (2013.01); *C08K 2201/01* (2013.01); *C08K 2201/011* (2013.01)

(58) Field of Classification Search
CPC ... C08F 2/46; C07C 255/54; C08J 3/28; C08J 3/247; C08J 2379/02; C08K 3/013; C08K 3/08; C08K 2003/0862; C08K 2003/0843; C08K 2003/0831; C08K 2003/085; C08K 3/20; C08K 3/22; C08K 2003/22687; C08K 2003/2265; C08K 2201/001; C08K 2201/011; C08K 2201/01; C08K 221/005
See application file for complete search history.

(56) References Cited

U.S. PATENT DOCUMENTS

| | | | |
|---|---|---|---|
| 4,408,035 A | 10/1983 | Keller | |
| 5,003,039 A | 3/1991 | Keller | |
| 5,003,078 A | 3/1991 | Keller | |
| 5,004,801 A | 4/1991 | Keller et al. | |
| 5,132,396 A | 7/1992 | Keller | |
| 5,139,054 A | 8/1992 | Long et al. | |
| 5,208,318 A | 5/1993 | Keller | |
| 5,237,045 A | 8/1993 | Burchill et al. | |
| 5,292,854 A | 3/1994 | Keller | |
| 5,350,828 A | 9/1994 | Keller et al. | |
| 8,222,403 B2 | 7/2012 | Laskoski et al. | |
| 8,329,936 B2 * | 12/2012 | Friese | ............... C07C 253/30 |
| | | | 558/442 |
| 8,920,670 B2 * | 12/2014 | Harada | ............... H01F 1/33 |
| | | | 252/62.55 |
| 2006/0194944 A1 | 8/2006 | Fowler et al. | |
| 2009/0230347 A1 * | 9/2009 | Pridohl | ............... C09J 9/00 |
| | | | 252/62.54 |
| 2011/0108755 A1 | 5/2011 | Laskoski et al. | |
| 2012/0249375 A1 | 10/2012 | Heino et al. | |
| 2013/0063296 A1 * | 3/2013 | Hennig | ............... H01Q 1/245 |
| | | | 342/1 |

FOREIGN PATENT DOCUMENTS

| | | |
|---|---|---|
| CN | 101271741 | 9/2008 |
| CN | 101463049 | 6/2009 |
| CN | 102067248 | 5/2011 |
| CN | 102775755 | 11/2012 |
| CN | 103834323 | 6/2014 |
| EP | 0696156 | 2/1996 |
| JP | S63199228 | 8/1988 |
| JP | 6089157 | 11/1994 |
| JP | 2791595 | 8/1998 |
| JP | 2008530309 | 8/2008 |
| KR | 1020050044409 | 5/2005 |
| KR | 100558158 | 3/2006 |
| KR | 1020070046043 | 5/2007 |
| KR | 1020110117138 | 10/2011 |
| KR | 1020140066612 | 6/2014 |
| KR | 1020160114358 | 10/2016 |

OTHER PUBLICATIONS

International Search Report of the International Searching Authority corresponding to International Patent Application No. PCT/KR2017/013782, dated Feb. 22, 2018. (2 Pages).

* cited by examiner

Primary Examiner — Jane L Stanley
(74) Attorney, Agent, or Firm — Myers Bigel, P.A.

(57) ABSTRACT

The present application relates to a curable composition. The present application provides a curable composition comprising an internal heat source for generating heat by application of an alternate-current magnetic field from the outside, together with a phthalonitrile compound and a curing agent therefor. The curable composition can precisely control the heat generated from the internal heat source according to the strength of the alternate-current magnetic field to precisely control curing conditions of the curable composition.

19 Claims, No Drawings

CURABLE COMPOSITION

CROSS REFERENCE TO RELATED APPLICATIONS

This application is a 35 U.S.C. § 371 national stage application of PCT International Application No. PCT/KR2017/013782, filed on Nov. 29, 2017, which claims priority from Korean Patent Application No. 10-2016-0162151 filed on Nov. 30, 2016, the contents of which are incorporated herein by reference in their entireties. The above reference PCT International Application was published in the Korean language as International Publication No. WO 2018/101728 A1 on Jun. 7, 2018.

TECHNICAL FIELD

The present application relates to a curable composition.

BACKGROUND ART

A phthalonitrile resin can be produced by applying a phthalonitrile compound and a curing agent therefor to a curing reaction, and the phthalonitrile resin thus produced can be used for various applications. For example, a composite formed by impregnating a filler such as glass fiber or carbon fiber with the phthalonitrile resin can be used as a material for automobiles, airplanes, ships, and the like. The process for producing the composite may include, for example, a process of mixing a mixture of phthalonitrile and a curing agent or a prepolymer formed by reaction of the mixture with a filler and then curing the mixture (see, for example, Patent Document 1).

In the production process of the phthalonitrile resin, as the above-mentioned curing reaction, a thermosetting method applied by a hot press or an oven and the like is adopted.

PRIOR ART DOCUMENTS

Patent Documents (Patent Document 1) Korean Patent No. 0558158

DISCLOSURE

Technical Problem

The present application relates to a curable composition. The present application provides a curable composition comprising an internal heat source for generating heat by application of an alternate-current magnetic field from the outside, together with a phthalonitrile compound and a curing agent therefor. The curable composition can precisely control the heat generated from the internal heat source according to the strength of the alternate-current magnetic field to precisely control curing conditions of the curable composition and accordingly the cure degree, thereby ultimately obtaining a resin having excellent physical properties.

Technical Solution

The curable composition of the present application may comprise a phthalonitrile compound, a curing agent for the phthalonitrile compound and magnetic particles. Here, the magnetic particles may be selected so as to generate heat by a magnetic reversal vibration phenomenon through an external alternate-current magnetic field.

In this specification, the magnetic particle may be otherwise referred to as a magnetic body, and in one example, may also be referred to as a nano-magnetic particle or a nano-magnetic body.

The curable composition may comprise a phthalonitrile compound and a curing agent. In the present application, the phthalonitrile compound and the curing agent may be contained as a main component in the curable composition. In the present application, the term main component may mean a case where the relevant component is contained in a weight ratio of about 55% or more, 60% or more, 65% or more, 70% or more, 75% or more, 80% or more, 85% or more, or 90% or more. Here, the upper limit of the ratio of the component contained as the main component is not particularly limited, which may be, for example, about 100% or less, or 99% or less. In addition, the ratios of the phthalonitrile compound and the curing agent are ratios in the solid content of the curable composition. Here, the term solid content is a state in which the curable composition substantially comprises no solvent, which may mean, for example, a curable composition in which the solvent is in a weight ratio of 5% or less, 4% or less, 3% or less, 2% or less, 1% or less, or 0.5% or less.

The kind of the phthalonitrile compound that can be included in the curable composition is not particularly limited.

For example, a compound comprising 1 or more, 2 or more, 2 to 20, 2 to 16, 2 to 12, 2 to 8, or 2 to 4 phthalonitrile structures which are capable of forming a phthalonitrile resin through reaction with a curing agent, can be used. There are various compounds known to be suitable for forming the phthalonitrile resin, and in the present application, all of the above known compounds can be used. In one example, as examples of the compounds, those known in U.S. Pat. Nos. 4,408,035, 5,003,039, 5,003,078, 5,004,801, 5,132,396, 5,139,054, 5,208,318, 5,237,045, 5,292,854 or U.S. Pat. No. 5,350,828 can be exemplified, and various compounds known in the art, besides those mentioned by above documents, can be included in the examples.

In one example, the phthalonitrile compound included in the curable composition may be in a monomeric form, an oligomeric form or a prepolymeric form and the like.

In one example, the phthalonitrile compound used in the present application may be exemplified by a compound represented by Formula 1, but is not limited thereto.

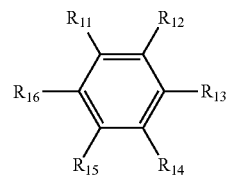

[Formula 1]

In Formula 1, $R_{11}$ to $R_{16}$ are each independently a hydrogen atom, an alkyl group, an alkenyl group, an alkynyl group, an alkoxy group, an aryl group, or a substituent of Formula 2 or 3 below. In Formula 1, at least one of $R_{11}$ to $R_{16}$ may be a substituent of Formula 2 or 3 below.

In one example, at least one, two or more, three or more, four or more, or five or more of $R_{11}$ to $R_{16}$ in Formula 1 may be a substituent of Formula 2 or 3 below.

At this time, the upper limit of the number of substituents of Formula 2 or 3 below is not particularly limited, which may be, for example, 10 or less, 9 or less, 8 or less, 7 or less, or 6 or less.

Substituents of Formula 2 or 3 in which at least two or two to three are present in Formula 1 may be present at ortho, meta or para positions relative to each other.

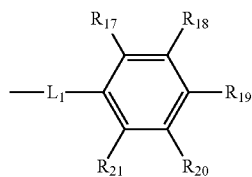

[Formula 2]

In Formula 2, $L_1$ is a single bond, an oxygen atom, a sulfur atom, $-S(=O)_2-$, a carbonyl group, an alkylene group, an alkenylene group, an alkynylene group, $-C(=O)-X_3-$ or $-X_3-C(=O)-$, where $X_3$ is an oxygen atom, a sulfur atom, $-S(=O)_2-$, an alkylene group, an alkenylene group or an alkynylene group, and $R_{17}$ and $R_{21}$ are each independently hydrogen, an alkyl group, an alkoxy group, an aryl group or a cyano group, provided that two or more or two of $R_{17}$ to $R_{21}$ are each a cyano group. Cyano groups in which at least two are present in Formula 2 may be present at ortho, meta or para positions relative to each other.

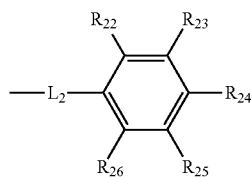

[Formula 3]

In Formula 3, $L_2$ is a single bond, an oxygen atom, a sulfur atom, $-S(=O)_2-$, a carbonyl group, an alkylene group, an alkenylene group, an alkynylene group, $-C(=O)-X_4-$ or $-X_4-C(=O)-$, where $X_4$ is an oxygen atom, a sulfur atom, $-S(=O)_2-$, an alkylene group, an alkenylene group or an alkynylene group, and $R_{22}$ and $R_{26}$ are each independently hydrogen, an alkyl group, an alkoxy group, an aryl group or a substituent of Formula 2 above, provided that at least one or one of $R_{22}$ to $R_{26}$ is a substituent of Formula 2 above. The substituent of Formula 2 which at least one is present in Formula 3 may exist at an ortho, meta or para position based on $L_2$.

When Formula 2 or 3 is present, $L_1$ of Formula 2 above may be linked to Formula 1 or 3, or $L_2$ of Formula 3 may be linked to Formula 1.

In this specification, the term alkyl group may mean an alkyl group having 1 to 20 carbon atoms, 1 to 16 carbon atoms, 1 to 12 carbon atoms, 1 to 8 carbon atoms or 1 to 4 carbon atoms, unless otherwise specified. The alkyl group may be a linear, branched or cyclic alkyl group and may be optionally substituted with one or more substituents.

In this specification, the term alkoxy group may mean an alkoxy group having 1 to 20 carbon atoms, 1 to 16 carbon atoms, 1 to 12 carbon atoms, 1 to 8 carbon atoms or 1 to 4 carbon atoms, unless otherwise specified. The alkoxy group may be a linear, branched or cyclic alkoxy group and may be optionally substituted with one or more substituents.

In this specification, the term alkenyl group or alkynyl group may mean an alkenyl group or alkynyl group having 2 to 20 carbon atoms, 2 to 16 carbon atoms, 2 to 12 carbon atoms, 2 to 8 carbon atoms or 2 to 4 carbon atoms, unless otherwise specified. The alkenyl group or alkynyl group may be linear, branched or cyclic and may be optionally substituted with one or more substituents.

In this specification, the term alkylene group may mean an alkylene group having 1 to 20 carbon atoms, 1 to 16 carbon atoms, 1 to 12 carbon atoms, 1 to 8 carbon atoms or 1 to 4 carbon atoms, unless otherwise specified. The alkylene group may be a linear, branched or cyclic alkylene group and may be optionally substituted with one or more substituents.

In this specification, the term alkenylene group or alkynylene group may mean an alkenylene group or alkynylene group having 2 to 20 carbon atoms, 2 to 16 carbon atoms, 2 to 12 carbon atoms, 2 to 8 carbon atoms or 2 to 4 carbon atoms, unless otherwise specified. The alkenylene group or alkynylene group may be linear, branched or cyclic and may be optionally substituted with one or more substituents.

In this specification, the term aryl group or arylene group may mean, unless otherwise specified, a monovalent residue or divalent residue derived from a compound comprising one benzene structure, or a structure in which two or more benzene rings are linked while sharing one or two carbon atoms, or linked by any linker, or a derivative thereof. The aryl group or arylene group may be, for example, an aryl group having 6 to 30 carbon atoms, 6 to 25 carbon atoms, 6 to 21 carbon atoms, 6 to 18 carbon atoms or 6 to 13 carbon atoms, unless otherwise specified.

In the present application, the substituent, with which the alkyl group, alkenyl group, alkynyl group, alkylene group, alkenylene group, alkynylene group, alkoxy group, aryl group, arylene group, and the like may be optionally substituted, may be exemplified by a hydroxy group, a halogen atom, a carboxyl group, a glycidyl group, an acryloyl group, a methacryloyl group, an acryloyloxy group, a methacryloyloxy group, a thiol group, an alkyl group, an alkenyl group, an alkynyl group, an alkylene group, an alkenylene group, an alkynylene group, an alkoxy group or an aryl group, and the like, but is not limited thereto.

The kind of the curing agent contained together with the phthalonitrile compound in the curable composition is not particularly limited as long as it can react with the phthalonitrile compound to form a polymer, and for example, if it is a compound known to be useful in the formation of a so-called phthalonitrile resin, any compound can also be used. The curing agent known to be suitable for the formation of the phthalonitrile resin can be exemplified by an aromatic amine compound, a phenol compound, an inorganic acid, an organic acid, a metal or a metal salt, but is not limited thereto.

In one example, an amine compound such as an aromatic amine compound or a hydroxy compound such as phenol may be used as a curing agent. In the present application, the hydroxy compound may mean a compound containing at least one or two hydroxy groups in the molecule. Curing agents capable of curing a phthalonitrile compound to form a resin are variously known, and these curing agents are mostly applicable in the present application.

In one example, a compound of Formula 4 can be used as a curing agent.

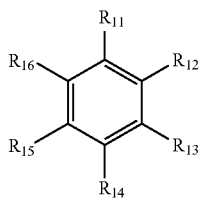

[Formula 4]

In Formula 4, $R_{11}$ to $R_{16}$ are each independently hydrogen, an alkyl group, an alkoxy group, an aryl group, an amine group or a substituent of Formula 5 below, provided that two or more of $R_{11}$ to $R_{16}$ are each an amine group or a substituent of Formula 5 below.

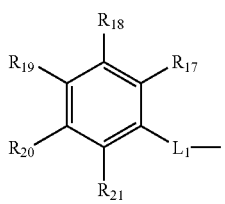

[Formula 5]

In Formula 5, $L_1$ is an alkylene group, an alkylidene group, an oxygen atom or a sulfur atom, and $R_{17}$ to $R_{21}$ are each hydrogen, an alkyl group, an alkoxy group, an aryl group or an amine group, provided that at least one of $R_{17}$ to $R_{21}$ is an amine group.

When the substituent of Formula 5 is present, $L_1$ in the above structure may be linked to a benzene ring of Formula 4.

In one example, the curing agent may be a compound wherein two of $R_{11}$ to $R_{16}$ in Formula 4 are each a substituent of Formula 5 above. In this case, two substituents of Formulas 5 above in Formula 4 may be a structure in which on the basis of any one of them, the other is present at an ortho, meta or para position. Also, in this case, any one of $R_{18}$ to $R_{20}$ in the substituent of Formula 5 may be an amine group.

The ratio of the curing agent in the curable composition is not particularly limited. The above ratio can be adjusted so that the desired curability can be ensured in consideration of, for example, the ratio or kind of the curable component such as the phthalonitrile compound contained in the composition. For example, the curing agent may be included in about 0.02 mol to 1.5 mol per mol of the phthalonitrile compound contained in the curable composition. However, the above ratio is only an example of the present application. Usually, the process window tends to become narrow if the ratio of the curing agent in the curable composition is high, while the curing property tends to become insufficient if the ratio of the curing agent is low, so that the suitable ratio of the curing agent can be selected in consideration of these points, and the like.

The curable composition comprises magnetic particles, and these magnetic particles can act as an internal heat source to cure the curable composition. As the magnetic particles, it may be advantageous to apply multi-domain magnetic particles in which two or more magnetic domains are formed. When the external magnetic field is not present, these magnetic particles are randomly arranged, and when the external magnetic field is applied, they can be magnetized by the direction of the applied magnetic field. Here, the meaning that magnetic domains are randomly arranged may mean a state that the magnetic directions existing in the magnetic domains are each different and are not aligned, and in this case, the net value of magnetization may be substantially close to zero and exist in a state without magnetism. When an external electromagnetic field is applied, magnetization may occur by aligning the magnetic directions of the magnetic domains Such a magnetic particle may be a super-paramagnetic particle, but is not limited thereto.

It is usually determined according to the particle diameter of the magnetic particle whether or not the magnetic particle has a multi-domain.

For example, when the magnetic particle has a particle diameter of at least a particle diameter Ds satisfying Equation 1 below, the magnetic particle may have a multi-domain.

$$D_s = 2\sqrt{\frac{9A}{\mu_0 M_s^2}\left[\ln\left(\frac{D_s}{a}\right) - 1\right]}$$ [Equation 1]

In Equation 1, $\mu_0$ is a magnetic permittivity constant in vacuum (1.26×10$^{-6}$ H/m), Ms is saturation magnetization (unit: A/m or emu/g) of the magnetic particles, A is exchange stiffness (unit: J/m) of the magnetic particles, and a is a lattice constant (unit m) of the magnetic particles.

In Equation 1 above, the saturation magnetization, the exchange stiffness and the lattice constant of the magnetic particles except for the magnetic permeability constant are changed according to the specific type of magnetic particles. Therefore, after checking each of the numerical values for the magnetic particles to be applied, the size of the magnetic particles is controlled to the Ds or more obtained by substituting the numerical values into Equation 1, whereby the magnetic particles having multi-domains can be formed.

From the Ds or more obtained according to Equation above, the magnetic particles are subjected to multi-domains, and thus, the magnetic particles applied in the present application can have a particle diameter of at least the particle diameter Ds. Here, the upper limit of the particle diameter of the magnetic particles is not particularly limited. Usually, as the particle diameter of the magnetic particles exceeds Ds, coercive force of the corresponding magnetic particles tends to decrease, where the magnetic particles applied in the present application can have a particle diameter within a range capable of having the coercive force to be described below.

When such magnetic particles are applied, the corresponding particles may not be agglomerated and exist in a uniformly dispersed state in the composition because they act similar to absence of magnetism when no external magnetic field is present.

The corresponding magnetic particles do not generate heat by a so-called eddy current or hysteresis loss, but may be selected so that the hysteresis loss of the magnetic particles themselves is small and only the saturation magnetization value is substantially present to be capable of generating vibrational heat. For example, the magnetic particles may be selected so that the magnetic particles are vibrated by the coercive force of the magnetic particles upon application of an external electromagnetic field, thereby generating heat.

The magnetic particle may comprise two or more magnetic domains. The term "magnetic domain" generally means a region in which magnetization directions are differently divided within the magnetic particle. In the present application, magnetic particles having two or more magnetic domains are strongly magnetized by an external alternate-current magnetic field to generate vibrational heat, and when the magnetic field is eliminated, the magnetic particles return to the original magnetic domains, whereby magnetic particles with low residual magnetization of hysteresis loss can be provided.

In one example, the magnetic particles may have a coercive force in a range of 1 to 200 kOe, 10 to 150 kOe, 20 to 120 kOe, 30 to 100 kOe, 40 to 95 kOe, or 50 to 95 kOe. The term "coercive force" may mean an intensity of the critical magnetic field required to reduce the magnetization of the magnetic particles to zero. The magnetic particles magnetized by an external magnetic field maintain a certain degree of magnetized state even if a magnetic field is removed, where the intensity of a magnetic field capable of making the magnetization degree to zero by applying a reverse magnetic field to the magnetic particles thus magnetized is referred to as a coercive force. The coercive force of the magnetic particles may be a criterion for distinguishing soft magnetic particles or hard magnetic particles, and the magnetic particles of the present application may be soft magnetic particles. By controlling the coercive force of the magnetic particles in the above range, the present application more easily realizes the magnetization reversal of the magnetic particles to generate vibrational heat to a desired degree in the present application, so that it can satisfy a desired degree of curing physical properties by uniform curing of the resin.

In the case where the numerical value mentioned in the present application is a numerical value which is changed according to the measurement temperature of the corresponding numerical value, the corresponding numerical value is measured at room temperature, unless otherwise stated. The term room temperature means a natural temperature without warming or cooling, and may be, for example, any one temperature within a range of about 10° C. to 30° C., or a temperature of about 23° C. or about 25° C. or so.

In one example, the magnetic particle has a saturation magnetization value at room temperature in a range of 20 to 150 emu/g, 30 to 130 emu/g, 40 to 100 emu/g, 50 to 90 emu/g, 50 to 85 emu/g or 50 to 80 emu/g. By being capable of controlling the magnetic particles to have a relatively large saturation magnetization value and thus generating heat by vibration between magnetic particles other than eddy currents, the present application can satisfy curing physical properties by uniform curing of the resin. In the present application, the measurement of physical properties of the magnetic particles can be calculated by VSM (Vibrating Sample Magnetometer). The VSM is a device that measures magnetization values of samples by recording the applied magnetic field applied by a Hall probe and recording the electromotive force obtained on applying vibration to the sample by Faraday's law. According to Faraday's law, it can be seen that if the N pole of a bar magnet is directed and pushed towards the coil, the galvanometer moves and the current flows through the coil. The resultant current is called induction current, which was made by induced electromotive force. The VSM is a method of detecting the induced electromotive force, which occurs on vibrating a sample by such a basic operation principle, in the search coil, to measure the magnetization value of the sample by this electromotive force. The magnetic characteristics of a material can be measured simply as functions of magnetic field, temperature and time, and quick measurement in a magnetic force of up to 2 Tesla and a temperature range of 2 K to 1273 K is possible.

In one example, the magnetic particles may have an average particle diameter in a range of 20 nm to 300 nm, 30 nm to 250 nm, 40 nm to 230 nm, or 45 nm to 220 nm. In another example, the average particle diameter of the magnetic particles may be about 10 nm or more, 20 nm or more, 30 nm or more, 40 nm or more, 50 nm or more, 60 nm or more, 70 nm or more, 80 nm or more, or 90 nm or more, and in some cases, may also be about 300 nm or less, 280 nm or less, 260 nm or less, 240 nm or less, 220 nm or less, 200 nm or less, 180 nm or less, 160 nm or less, 140 nm or less, or 120 nm or less. The magnetic domains in the magnetic particles may have an average size in a range of 10 to 50 nm or 20 to 30 nm. The present application can generate heat capable of uniformly curing the resin in the composition by controlling the number of magnetic domains and the magnitude of the coercive force of the magnetic particles to an appropriate range in the particle size range. The present application can generate sufficient vibrational heat on curing through a low coercive force and a large number of magnetic domains by controlling the size of the particles to 20 nm or more, and allow only the saturation magnetization value to be present while reducing hysteresis loss of the magnetic particles themselves, thereby realizing uniform and stable curing by controlling the particle size to 300 nm or less.

The material of the magnetic particles of the present application is not particularly limited as long as it can generate heat through electromagnetic induction heating. In one example, the magnetic particles may be particles represented by Formula 6 below.

$$MX_aO_b \qquad \text{[Formula 6]}$$

In Formula 6, M is a metal or a metal oxide, X is Fe, Mn, Co, Ni or Zn, and $|a \times c| = |b \times d|$ is satisfied, where c is the cation charge of X, and d is the anion charge of oxygen. In one example, M may be Fe, Mn, Mg, Ca, Zn, Cu, Co, Sr, Si, Ni, Ba, Cs, K, Ra, Rb, Be, Li, Y, B, or an oxide thereof. For example, when $X_aO_b$ is $Fe_2O_3$, c may be +3 and d may be −2. Also, for example, when $X_aO_b$ is $Fe_3O_4$, it can be expressed as $FeOFe_2O_3$, so that c may be +2 and +3, respectively, and d may be −2. The magnetic particles of the present application are not particularly limited as long as they satisfy Formula 6 above, and may be, for example, $MFe_2O_3$.

In one example, the composition of the present application may comprise, as magnetic particles, a compound of Formula 6 above alone, or a mixture of compounds of Formula 6 or a compound doping a compound of Formula 6 with an inorganic substance. The inorganic substance may comprise a monovalent to trivalent cationic metal or an oxide thereof, and two or more of plural cationic metals may be used.

The magnetic particles may comprise those having surface-treated particle surfaces. That is, the composition of the present application may comprise particles surface-treated with a metal, a metal oxide, an organic substance or an inorganic substance on the surface of the magnetic particles. The present application can prevent the magnetic particles from losing the coercive force of the magnetic particles by oxidation in air through the surface treatment. Furthermore, the surface treatment can improve compatibility with the filler, the dispersant organic solvent and the like to be described below, and improve dispersibility of the composition. In one example, the surface treatment can form a polymer of polymethyl methacrylate (PMMA) on the surface by attaching a methyl methacrylate (MMA) monomer to a magnetic particle having a carboxyl group on its surface. In addition, the surface treatment can be carried out by being subjected to an acid treatment to remove the oxide film on the surface, and the surface treatment can be also carried out through a method of coating silica particles.

In an embodiment of the present application, the magnetic particles may form magnetic particle clusters. By forming the nanoclusters, the nanoparticle-sized magnetic particles can prevent agglomeration between the magnetic particles and improve dispersibility, thereby effectively curing the resin by vibrational heat.

The ratio of the magnetic particles in the curable composition of the present application is not particularly limited, which may be selected in consideration of the heat required for curing the curable composition, and the like. In one example, the curable composition comprises 0.01 to 25 parts by weight, 0.1 to 20 parts by weight, 1 to 15 parts by weight, 3 to 13 parts by weight or 5 to 12 parts by weight of magnetic particles relative to 100 parts by weight of the phthalonitrile compound. In this specification, the unit "part by weight" means a weight ratio between the respective components.

The curable composition may also contain any other additives, if desired. As the substance that can be further contained in the curable composition, conductive particles can be exemplified. These conductive particles can be selected so that Joule heat can be generated by a so-called eddy current through application of an external alternate-current magnetic field.

In one example, the above-described magnetic particles are selected so that the vibrational heat may be generated in the low magnetic field region and the conductive particles are selected so that the Joule heat may be generated in the high magnetic field region. By this selection, the amount of heat generated by the application of the alternate-current magnetic field can be more precisely controlled and more heat can be generated, a working region (process window) upon curing can be secured widely, as compared with the case where the respective particles are applied alone.

In the present application, the term conductive particles may mean conductive particles having a conductivity at 20° C. of about 8 MS/m or more, 9 MS/m or more, 10 MS/m or more, 11 MS/m or more, 12 MS/m or more, 13 MS/m or more, or 14.5 MS/m or more. The upper limit of the conductivity is not particularly limited, which may be, for example, about 30 MS/m or less, 25 MS/m or less, or 20 MS/m or less.

When the conductive particles are metal particles, the relevant metal particles may be single metal particles or alloy metal particles.

Such conductive particles can generate Joule heat by a so-called eddy current through the application of an external alternate-current magnetic field. In some cases, the intensity of the alternate-current magnetic field that the above-described magnetic particles generate vibrational heat and the intensity of the alternate-current magnetic field to generate the Joule heat can be adjusted differently.

As the conductive particles, particles having an average particle diameter within a range of about 5 μm to 500 μm may be used. In such a particle diameter range, the desired generation efficiency of Joule heat can be increased. In another example, the average particle diameter may be about 7 μm or more, or about 9 μm or more. In another example, the average particle diameter may be about 450 μm or less, about 400 μm or less, about 350 μm or less, about 300 μm or less, about 250 μm or less, about 200 μm or less, about 150 μm or less, 100 μm or less, 90 μm or less, 80 μm or less, 70 μm or less, 60 μm or less, 50 μm or less, 40 μm or less, 30 μm or less, or 20 μm or less. As the conductive particles in the curable composition, those having different average particle diameters from each other may also be applied.

As the conductive particles, an appropriate kind may be selected and applied without any particular limitation as long as it has the above-described conductivity and particle diameter.

An example of conductive particles, for example, conductive metal particles may be exemplified by nickel, iron, cobalt, silver, copper, gold, aluminum, calcium, tungsten, zinc, lithium, iron, platinum, tin, lead, titanium, manganese, magnesium or chromium, and the like, but is not limited thereto.

In one example, the conductive particles having a proper relative magnetic permeability can be selected. This selection makes it possible to further improve the generation efficiency of heat by induction heating.

For example, as the conductive particles, the particles having a relative magnetic permeability of 90 or more may be used. Here, the relative magnetic permeability ($\mu_r$) is a ratio ($\mu/\mu_0$) of the magnetic permeability ($\mu$) of the relevant material to the magnetic permeability ($\mu_0$) in the vacuum. The particles used in the present application may have a relative magnetic permeability of 95 or more, 100 or more, 110 or more, 120 or more, 130 or more, 140 or more, 150 or more, 160 or more, 170 or more, 180 or more, 190 or more, 200 or more, 210 or more, 220 or more, 230 or more, 240 or more, 250 or more, 260 or more, 270 or more, 280 or more, 290 or more, 300 or more, 310 or more, 320 or more, 330 or more, 340 or more, 350 or more, 360 or more, 370 or more, 380 or more, 390 or more, 400 or more, 410 or more, 420 or more, 430 or more, 440 or more, 450 or more, 460 or more, 470 or more, 480 or more, 490 or more, 500 or more, 510 or more, 520 or more, 530 or more, 540 or more, 550 or more, 560 or more, 570 or more, 580 or more, or 590 or more. The upper limit of the relative magnetic permeability is not particularly limited because the higher the value is, the higher the heat is generated when the electromagnetic field for induction heating as described below is applied. In one example, the upper limit of the relative magnetic permeability may be, for example, about 300,000 or less.

The ratio of the conductive particles in the curable composition of the present application is not particularly limited, which may be selected in consideration of the heat required for curing the curable composition, and the like. In one example, the curable composition may comprise 0.01 to 25 parts by weight, 0.1 to 20 parts by weight, 1 to 15 parts by weight, 3 to 13 parts by weight or 5 to 12 parts by weight of the conductive particles relative to 100 parts by weight of the phthalonitrile compound.

In one example, when the conductive particles are included, the ratio can be adjusted in a range lower than the magnetic particles.

The curable composition may further comprise, in addition to the components described above, any additives required in the curable composition. Such an additive may be exemplified by a curing agent, an antioxidant, a radical-generating material, an organic or inorganic pigment or dye, a dispersant, a filler, a functional polymer or a light stabilizer, and the like, but is not limited thereto.

As an example of additives that may be included in the curable composition, various fillers may be exemplified. The kind of the material that can be used as the filler is not particularly limited, and any known filler suitable for the intended use may be used. Exemplary fillers include a metal material, a ceramic material, glass, a metal oxide, a metal nitride or a carbon-based material, but are not limited thereto. In addition, the form of the filler is also not particularly limited and may be various forms, such as fibrous materials such as aramid fibers, glass fibers, carbon fibers or ceramic fibers, or woven fabrics, nonwoven fabrics, cords or strings, formed by the material, particles containing nanoparticles, polygons or other amorphous forms. As an example of the carbon-based material, graphite, graphene, or carbon nanotubes, and the like, or derivatives or isomers such as their oxides, and the like may be exemplified.

The present application also relates to a prepolymer formed by the curing reaction of the curable composition.

In the present application, the term prepolymer state may mean a state in which the reaction of the phthalonitrile compound with the curing agent occurs in the curable composition to some extent (for example, a stage in which the polymerization of a so-called A or B stage step occurs), or a state which does not reach the fully polymerized state and exhibits appropriate fluidity, and thus, for example, is possible to process the composite, as described below. In one example, the prepolymer state may mean a state in which the polymerization of the curable composition proceeds to some extent.

The prepolymer can also exhibit excellent curability, an adequate processing temperature and a wide process window. In addition, the prepolymer can exhibit stability over time even when it is stored at room temperature for a long period of time.

For example, the processing temperature, for example, the glass transition temperature or the melting temperature, of the prepolymer may be 150° C. or lower. In another example, the processing temperature may be about 140° C. or lower, about 130° C. or lower, about 120° C. or lower, about 110° C. or lower, about 100° C. or lower, about 90° C. or lower, about 80° C. or lower, about 70° C. or lower, about 60° C. or lower, or about 50° C. or lower, and may also be about −20° C. or higher, about −10° C. or higher, or about 0° C. or higher. In this case, the absolute value of the difference (Tc−Tp) between the processing temperature Tp of the prepolymer and the curing temperature Tc of the prepolymer may be 50° C. or more, 70° C. or more, or 100° C. or more. In one example, the curing temperature Tc may be higher than the processing temperature Tp. Such a range may be advantageous for securing appropriate processability in the process of preparing a complex to be described later, for example, using the prepolymer. The upper limit of the process window is not particularly limited. For example, the absolute value of the difference (Tc−Tp) between the processing temperature Tp and the curing temperature Tc may be 300° C. or less or 200° C. or less.

The prepolymer may further comprise any known additives in addition to the above components. As an example of such an additive, the above-mentioned fillers and the like may be exemplified, without being limited thereto.

The present application also relates to a composite. The composite may comprise the above-described phthalonitrile resin and the filler. The composite thus formed may comprise the phthalonitrile resin and the filler, and may be applied to various applications including durables for automobiles, airplanes, ships, and the like.

The kind of the filler is not particularly limited and may be suitably selected in consideration of the intended use. The usable filler may be exemplified by the kind already described, but it not limited thereto.

Also, the ratio of the filler is not particularly limited, and may be set in an appropriate range according to the intended use.

The present application also relates to a precursor for preparing the composite, wherein the precursor may comprise, for example, the curable composition described above and the filler, or the prepolymer described above and the filler.

The composite can be prepared in a known manner using the precursor. For example, the composite can be formed by curing the precursor.

The present application also relates to a method for curing such a curable composition. By such a curing process, the above-described prepolymer or composite can be formed. In one example, the curing of the curable composition can be performed by an induction heating method.

As described above, since the curable composition comprises magnetic particles, the induction heating method can be applied thereto.

When the alternate-current magnetic field is applied through the induction heating, the vibrational heat of the magnetic particles can be generated according to the intensity of the applied alternate-current magnetic field, and a uniform cured product can be formed in a short time by the heat of the particles uniformly dispersed in the composition.

The curing process may comprise a step of applying an alternate-current magnetic field to the curable composition. By the application of the alternate-current magnetic field, vibrational heat of the magnetic particles is generated, whereby the composition can be cured. At this time, the conditions for applying the alternate-current magnetic field are not particularly limited as they are determined depending on the kind and ratio of the particles in the curable composition, the amount of heat required for curing, and the like. For example, the induction heating can be performed by applying an alternate-current magnetic field using an induction heater formed in the form of a coil or the like.

Here, the alternate-current magnetic field may be applied at an intensity in a range of, for example, 0.001 to 0.5 Tesla (Wb/m$^2$). In another example, the magnitude of the applied alternate-current magnetic field may be 0.45 Tesla or less, 0.4 Tesla or less, 0.35 Tesla or less, 0.3 Tesla or less, 0.25 Tesla or less, 0.2 Tesla or less, 0.15 Tesla or less, 0.1 Tesla or less, 0.05 Tesla or less, or 0.045 Tesla or less. In another example, the intensity of the alternate-current magnetic field may be about 0.002 Tesla or more, about 0.003 Tesla or more, about 0.004 Tesla or more, 0.005 Tesla or more, 0.01 Tesla or more, 0.015 Tesla or more, or 0.02 Tesla or more.

The induction heating can be performed, for example, at a frequency of about 10 kHz to 1,000 kHz. In another example, the frequency may be 900 kHz or less, 800 kHz or less, 700 kHz or less, 600 kHz or less, 500 kHz or less, or 450 kHz or less. In another example, the frequency may be about 150 kHz or more, about 200 kHz or more, or about 250 kHz or more.

The application of the alternate-current electromagnetic field for the induction heating can be performed within a range of, for example, about 5 seconds to 10 hours. In another example, the application time may be about 9 hours or less, about 8 hours or less, about 7 hours or less, about 6 hours or less, about 5 hours or less, about 4 hours or less, about 3 hours or less, about 2 hours or less, about 1 hour or less, about 50 minutes or less, about 40 minutes or less, or about 30 minutes or less. Also, in another example, the application time may be about 1 minute or more, about 5 minutes or more, about 10 minutes or more, or about 15 minutes or more.

In addition, the curing process may be performed in multiple steps. For example, the production method may comprise a first step of applying an alternate-current magnetic field to the curable composition; and a second step of applying an alternate-current magnetic field to the curable composition under conditions different from those of the first step following the first step, and may also further comprise a third step or more steps of applying an alternate-current magnetic field in different conditions.

In one example, the fact that application conditions are different means a case where the intensity and/or application time of the applied alternate-current magnetic field are different from each other.

As described above, the above-mentioned induction heating conditions, for example, the applied alternate-current magnetic field, frequency and application time, and the like can be changed in consideration of the amount of heat required for curing of the curable composition, the kind and ratio of particles, and the like.

The curing of the curable composition may be performed only by the above-mentioned induction heating or, if necessary, may also be performed while applying appropriate heat with the application of the induction heating, i.e. the application of the alternate-current magnetic field.

Advantageous Effects

The present application provides a curable composition comprising an internal heat source for generating heat by application of an alternate-current magnetic field from the outside, together with a phthalonitrile compound and a curing agent therefor. The curable composition can precisely control the heat generated from the internal heat source according to the strength of the alternate-current magnetic field to precisely control curing conditions of the curable composition and accordingly the cure degree, thereby ultimately obtaining a resin having excellent physical properties.

Mode for Invention

Hereinafter, the present application will be specifically described by way of examples and comparative examples, but the scope of the present application is not limited to the following examples.

1. DSC (Differential Scanning Calorimetry) Analysis

DSC analysis was performed using a Q20 system from TA instrument. The measurement was performed in a $N_2$ flow atmosphere while raising the temperature from 35° C. to 400° C. at a heating rate of 10° C./min, and the calorific values of a specimen before and after curing were measured, whereby the cure degree was determined according to Equation below.

<Cure Degree Determination Equation>

Cure degree=1−(calorific value of specimen after curing/calorific value of sample before curing)

2. TGA (Thermogravimetric Analysis) Analysis

TGA analysis was performed using a TGA e850 instrument from Mettler-Toledo. The measurement was analyzed in a $N_2$ flow atmosphere while raising the temperature of the compositions of Examples or Comparative Examples from 25° C. to 900° C. at a heating rate of 10° C./min.

EXAMPLE 1

A compound represented by Formula A was melted on a hot plate at 240° C. for 10 minutes using an aluminum dish. A curing agent (1,3-bis(3-aminophenoxy)benzene) was added to the completely molten compound in a ratio of about 0.15 mol per mol of the above compound, further uniformly mixed on a hot plate at 240° C. for 10 minutes and cooled to prepare a polymerizable composition in the form of a prepolymer.

The prepared prepolymer was pulverized and prepared in the form of a fine powder, followed by mixing a nano-magnetic body at a ratio of about 10 wt %.

As the nano-magnetic body, Mn-ferrite having a saturation magnetization value of about 76 emu/g and a coercive force of about 89 kOe was used, and the particle diameter of the magnetic body was about 100 nm.

The polymerizable composition, in which the nano-magnetic body was mixed, was cured by applying a magnetic field thereto. The curing was performed in two steps, where the magnetic field application conditions and time at each step were summarized in Table 1 below. Also, the application of the magnetic field was performed using an easyheat 830 from Ambrell as a power supply, and a 5-turns pan-cake type coil having a diameter of about 50 mm was used as the working coil.

While the intensity of the alternate-current magnetic field was confirmed by monitoring the temperature inside the coil with a thermal imaging camera, the curing conditions were controlled by the intensity of the applied current and the application time.

[Formula A]

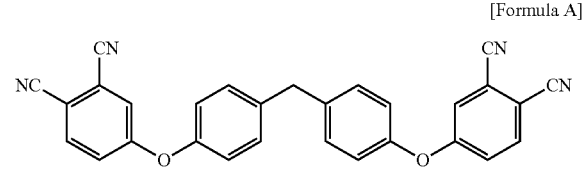 [SMILES: N#Cc1ccc(Oc2ccc(Cc3ccc(Oc4ccc(C#N)c(C#N)c4)cc3)cc2)cc1C#N]

EXAMPLE 2

The curing was performed in the same manner as in Example 1, except that the curing conditions were adjusted as shown in Table 1 below.

EXAMPLE 3

The curing was performed in the same manner as in Example 1, except that the curing conditions were adjusted as shown in Table 1 below.

EXAMPLE 4

The curing was performed in the same manner as in Example 1, except that the curing conditions were adjusted to three steps as shown in Table 1 below.

EXAMPLE 5

The curing was performed in the same manner as in Example 1, except that Mn—Mg-St-ferrite having a saturation magnetization value of about 55 emu/g, a coercive force of about 73 kOe and a particle diameter of about 100 nm was used as the nano-magnetic body, and the curing conditions were adjusted as shown in Table 1 below.

Comparative Example 1

The compound of Formula A used in Example 1 was melted on a hot plate at 240° C. for 10 minutes using an aluminum dish. A curing agent (1,3-bis(3-aminophenoxy) benzene) was added to the molten compound in a ratio of about 0.15 mol per mol of the above compound. The composition, to which the curing agent was added, was further uniformly mixed on a hot plate at 240° C. for 10 minutes and then cooled to prepare a polymerizable composition in the form of a prepolymer. The composition was cured by holding it in a hot press at 250° C. for 5 minutes and holding it again at 260° C. for 15 minutes.

Comparative Example 2

The polymerizable composition prepared in the same manner as in Comparative Example 1 was cured by holding it in a hot press at 250° C. for 5 minutes and holding it again at 300° C. for 15 minutes.

The measurement results of Examples and Comparative Examples above are shown in Table 1 below.

TABLE 1

| | | | Example | | | | | Comparative Example | |
|---|---|---|---|---|---|---|---|---|---|
| | | | 1 | 2 | 3 | 4 | 5 | 1 | 2 |
| Curing Conditions | Step 1 | Intensity | 25 | 25 | 25 | 25 | 25 | 250° C. | 250° C. |
| | | Time | 5 min | 5 min | 5 min | 5 min | 5 min | 5 min | 5 min |
| | | Frequency | 312 | 312 | 312 | 312 | 312 | — | — |
| | Step 2 | Intensity | 37.5 | 37.5 | 37.5 | 37.5 | 37.5 | 260° C. | 300° C. |
| | | Time | 5 min | 10 min | 15 min | 10 min | 15 min | 15 min | 15 min |
| | | Frequency | 309 | 309 | 309 | 309 | 309 | — | — |
| | Step 3 | Intensity | — | — | — | 40 | — | — | — |
| | | Time | — | — | — | 3 min | — | — | — |
| | | Frequency | — | — | — | 308 | — | — | — |
| | Total curing time | | 10 min | 15 min | 20 min | 18 min | 20 min | 20 min | 20 min |
| Cure degree (%) | | | 58% | >95% | >95% | >95% | >95% | 68% | 68% |
| 5% Decomposition temperature (° C.) | | | 484 | 485 | 485 | 485 | 484 | 483 | 485 |
| 10% Decomposition temperature (° C.) | | | 526 | 525 | 532 | 527 | 525 | 524 | 527 |

Intensity: intensity of the applied magnetic field in the case of Examples (unit: mTesla), and application temperature in the case of Comparative Examples
Frequency unit: kHz As confirmed from Table 1, according to the method of the present application, it can be confirmed that a phthalonitrile resin having excellent cure degree and heat resistance characteristics is obtained. Particularly, as can be seen from the comparison of Example 1 with the other Examples and Comparative Examples 1 and 2, according to the conventional method, there is a limit in increasing the cure degree achieved even when the temperature of the curing heat source is increased, while according to the method of the present application, the cure degree can be greatly increased by controlling the curing conditions, whereby it can be confirmed that the freedom degree for controlling the cure degree can be greatly improved.

The invention claimed is:

1. A curable composition comprising a phthalonitrile compound, a curing agent of the phthalonitrile compound, and magnetic particles having a particle diameter in a range of 20 nm to 300 nm, wherein the phthalonitrile compound is a compound of Formula 1 or a prepolymer comprising the compound of Formula 1:

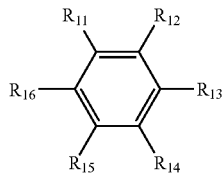

[Formula 1]

wherein, $R_{11}$ to $R_{16}$ are each independently a hydrogen atom, an alkyl group, an alkenyl group, an alkynyl group, an alkoxy group, an aryl group, or a substituent of Formula 2 or 3, and at least one of $R_{11}$ to $R_{16}$ is a substituent of Formula 3:

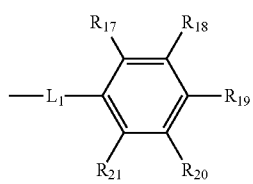

[Formula 2]

wherein, $L_1$ is a single bond, an oxygen atom, a sulfur atom, —S(=O)$_2$—, a carbonyl group, an alkylene group, an alkenylene group, an alkynylene group, —C(=O)—X$_3$— or —X$_3$—C(=O)—, wherein X$_3$ is an oxygen atom, a sulfur atom, —S(=O)$_2$—, an alkylene group, an alkenylene group or an alkynylene group, and $R_{17}$ to $R_{21}$ are each independently hydrogen, an alkyl group, an alkoxy group, an aryl group or a cyano group, and two or more of $R_{17}$ to $R_{21}$ are each a cyano group:

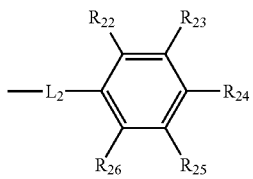

[Formula 3]

wherein, $L_2$ is a single bond, an oxygen atom, a sulfur atom, $-S(=O)_2-$, a carbonyl group, an alkylene group, an alkenylene group, an alkynylene group, $-C(=O)-X_4-$ or $-X_4-C(=O)-$, wherein $X_4$ is an oxygen atom, a sulfur atom, $-S(=O)_2-$, an alkylene group, an alkenylene group or an alkynylene group, and $R_{22}$ to $R_{26}$ are each independently hydrogen, an alkyl group, an alkoxy group, an aryl group or a substituent of Formula 2, and at least one of $R_{22}$ to $R_{26}$ is a substituent of Formula 2.

2. The curable composition according to claim 1, wherein the magnetic particles are multi-domain type magnetic particles.

3. The curable composition according to claim 2, wherein the magnetic particles comprise magnetic domains, and
wherein the magnetic domains in the magnetic particles have an average size in a range of 10 to 50 nm.

4. The curable composition according to claim 1, wherein the magnetic particles have the particle diameter equal to or greater than Ds satisfying Equation 1:

$$D_s = 2\sqrt{\frac{9A}{\mu_0 M_S^2}\left[\ln\left(\frac{D_s}{a}\right) - 1\right]}$$ [Equation 1]

wherein, $\mu_0$ is a magnetic permittivity constant in vacuum, $M_s$ is saturation magnetization of the magnetic particles, A is exchange stiffness of the magnetic particles, and a is a lattice constant of the magnetic particles.

5. The curable composition according to claim 1, wherein the magnetic particles have a coercive force in a range of 1 to 200 kOe.

6. The curable composition according to claim 1, wherein the magnetic particles have a saturation magnetization value in a range of 20 to 150 emu/g.

7. The curable composition according to claim 1, wherein the magnetic particles are Formula 6 below:

$MX_aO_b$ [Formula 6]

wherein, M is a metal or a metal oxide, X is Fe, Mn, Co, Ni or Zn, and $|a \times c| = |b \times d|$ is satisfied, wherein c is a cation charge of X, and d is an anion charge of oxygen.

8. The curable composition according to claim 7, wherein M is Fe, Mn, Mg, Ca, Zn, Cu, Co, Sr, Si, Ni, Ba, Cs, K, Ra, Rb, Be, Li, Y, B or an oxide thereof.

9. The curable composition according to claim 1, further comprising conductive particles having a conductivity at 20° C. of 8 MS/m or more.

10. The curable composition according to claim 9, wherein the conductive particles are nickel, iron, cobalt, silver, copper, gold, aluminum, calcium, tungsten, zinc, lithium, iron, platinum, tin, lead, titanium, manganese, magnesium or chromium particles.

11. The curable composition according to claim 9, wherein the conductive particles have a relative magnetic permeability of 90 or more.

12. The curable composition according to claim 1, wherein a mole ratio of the phthalonitrile compound to the curing agent is about 1:0.02 to 1:1.5.

13. The curable composition according to claim 1, wherein the curing agent of the phthalonitrile compound comprises 1,3-bis(3-aminophenoxy)benzene.

14. The curable composition according to claim 1, further comprising a filler.

15. A method for producing a phthalonitrile resin comprising a step of applying an alternate-current magnetic field to the curable composition of claim 1 to induce a curing reaction between the phthalonitrile compound and the curing agent by heat generated by induction heating of the magnetic particles.

16. The method for producing the phthalonitrile resin according to claim 15, comprising:
a first step of applying a first alternate-current magnetic field having a first frequency to the curable composition for a first duration of time; and
a second step of applying a second alternate-current magnetic field having a second frequency to the curable composition for a second duration of time, wherein the first frequency is different from the second frequency, and/or the first duration of time is different from the second duration of time.

17. The method for producing the phthalonitrile resin according to claim 15, wherein the phthalonitrile compound in the curable composition is in a prepolymer form.

18. The method for producing the phthalonitrile resin according to claim 15, wherein the alternate-current magnetic field has an intensity in a range of 1 to 500 mTesla during induction heating.

19. The method for producing the phthalonitrile resin according to claim 15, wherein the alternate-current magnetic field has a frequency in a range of 10 kHz to 1,000 kHz during induction heating.